United States Patent
Hori et al.

[11] Patent Number: 5,824,808
[45] Date of Patent: Oct. 20, 1998

[54] CYCLIC PHENOL SULFIDE AND PROCESS FOR PRODUCING THE SAME

[75] Inventors: Takashi Hori; Hitoshi Kumagai; Mitsuharu Hasegawa; Yoko Sato; Hiroshi Munakata; Yoshihiro Sugawa, all of Saitama, Japan

[73] Assignees: Cosmo Research Institute; Cosmo Oil Co., Ltd., both of Tokyo, Japan

[21] Appl. No.: 614,969

[22] Filed: Mar. 11, 1996

[30] Foreign Application Priority Data

Mar. 10, 1995 [JP] Japan ................................. 7-078459
Dec. 18, 1995 [JP] Japan ................................. 7-347503
Mar. 4, 1996 [JP] Japan ................................. 8-070902

[51] Int. Cl.⁶ ............... C07D 331/02; C07D 327/00; C07D 339/00; C08G 65/38
[52] U.S. Cl. ............... 549/1; 549/2; 549/11; 528/212
[58] Field of Search ............ 549/1, 2, 11; 528/212

[56] References Cited

U.S. PATENT DOCUMENTS

| | | | |
|---|---|---|---|
| 1,757,400 | 5/1930 | Thauss | 528/212 |
| 1,922,467 | 8/1933 | Bergdolt et al. | 528/212 |
| 2,198,828 | 4/1940 | Lieber et al. | 528/212 |
| 3,468,961 | 9/1969 | Geering et al. | 568/64 |
| 3,621,032 | 11/1971 | Ariyan | 549/11 |
| 3,668,258 | 6/1972 | Hageman | 528/212 |
| 3,769,342 | 10/1973 | Ariyan et al. | 549/11 |
| 3,925,414 | 12/1975 | Landis et al. | 549/11 |
| 4,089,877 | 5/1978 | Klinger et al. | 549/11 |
| 4,259,464 | 3/1981 | Burikes et al. | 525/480 |
| 4,339,590 | 7/1982 | Yamazaki et al. | 549/11 |
| 4,933,407 | 6/1990 | Harris et al. | 526/208 |
| 5,206,437 | 4/1993 | Morita | 564/310 |

OTHER PUBLICATIONS

Ariyan et al, "Action of Sulfur monochloride on aromatic ethers", CA58:6731e.

J. Chem. Soc., 1962, pp. 4609–4712, XP000568857, Z.S. Ariyan et al, p. 4711, line 31–line 37.

Yoshihiro Ohba, et al. "Synthesis of Sulfur–Bridged Analogs of Calix[4]Arene", 2–4 Jun. 1993, pp. PS/B–36.

*Primary Examiner*—Deborah C. Lambkin
*Attorney, Agent, or Firm*—Sughrue, Mion, Zinn, Macpeak & Seas, PLLC

[57] ABSTRACT

A cyclic phenol sulfide represented by the following formula (1) is described:

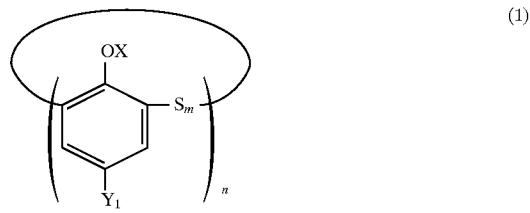

(1)

wherein X represents a hydrogen atom, a hydrocarbon group, or an acyl group; $Y_1$ represents a hydrogen atom, a hydrocarbon group, a halogenated hydrocarbon group, $-COR^1$, $-OR^2$, $-COOR^3$, $-CN$, $-CONH_2$, $-NO_2$, $-NR^4R^5$, a halogen atom, $-SO_4R^6$, or $-SO_3R^7$, in which $R^{11}$, $R^2$, $R^3$, $R^4$, $R^5$, $R^6$, and $R^7$ each represents a hydrogen atom or a hydrocarbon group; n is an integer of 3 or more; and m is an integer of 1 to 7, provided that the plural m's of the $S_m$'s are the same or different; the plural X's are the same or different; and the plural $Y_1$'s are the same or different. A process for producing the cyclic phenol sulfide is also described.

29 Claims, No Drawings

CYCLIC PHENOL SULFIDE AND PROCESS FOR PRODUCING THE SAME

FIELD OF THE INVENTION

The present invention relates to a novel cyclic phenol sulfide which can be used as, e.g., an antioxidant, catalyst, metal-trapping agent, light sensor, ion sensor, sensor with substrate specificity, separating-membrane material, polymer material, phase-transfer catalyst, synthetic enzyme, light energy converter, or an intermediate for functional molecules using a recognition ability of an ion or molecule. The present invention also relates to a process for producing the phenol sulfide.

BACKGROUND OF THE INVENTION

Alkylphenol sulfides are conventionally known as an antioxidant (e.g., U.S. Pat. Nos. 2,239,534, 3,377,334), a sulfurizing agent for rubbers (e.g., U.S. Pat. Nos. 3,468,961, 3,647,885), a polymer stabilizer (e.g., U.S. Pat. Nos. 3,882,082, 3,845,013, 3,843,600), an anticorrosive (e.g., U.S. Pat. No. 3,684,587), and a starting material for phenates for use as a lubricating-oil additive (Hori et al., Sekiyu Gakkai-shi, Vol. 34, p. 446, 1991).

Known processes for producing conventional phenol sulfides include a method in which a phenol and elemental sulfur are used as starting materials (e.g., A. J. Neale et al., Tetrahedron, Vol. 25 (1969), p. 4593); a method in which a phenol, elemental sulfur, and a base catalyst are used as starting materials (e.g., U.S. Pat. No. 3,468,961); a method in which a phenol, elemental sulfur, and a molecular halogen are used as starting materials (e.g., B. Hortling et al., Polym. Bull., Vol. 8 (1982), p.1); a method in which a phenol reacts with an aryl disulfide in the presence of a base catalyst (e.g., T. Fujisawa et al., J. Org. Chem., Vol. 33 (1973), p.687); a method in which a phenol and a sulfur halide are used as starting materials (e.g., U.S. Pat. No. 2,239,534); and a method in which a halogenated phenol reacts with a sulfurized alkali metal reagent.

However, the references cited above each discloses an oligomer containing a 2,2'-thiobis(4-alkylphenol) (dimer), a 2-[3-(2-hydroxy-5-alkylphenylthio)-2-hydroxy-5-alkylphenylthio]-4-alkylphenol (trimer), or a 2-[3-[3-(2-hydroxy-5-alkylphenylthio)-2-hydroxy-5-alkylphenylthio]-2-hydroxy-5-alkylphenylthio]-4-alkylphenol (tetramer), or a composition containing such an oligomer and a process for the production thereof. Namely, the alkylphenol sulfides dealt with in those references are all non-cyclic compounds, and the existence of a cyclic phenol sulfide and a method for producing the same have not been disclosed.

SUMMARY OF THE INVENTION

An object of the present invention is to provide a novel cyclic phenol sulfide comprising at least three phenol structures as a basic structure which is a compound quite different from any of the conventionally existing non-cyclic dimers or trimers of alkylphenol sulfides or compositions of such oligomers.

Another object of the present invention is to provide a process for producing the cyclic phenol sulfide.

To accomplish the above objects, the present inventors made investigations on sulfurization reactions of various phenols. As a result, it has been found that the cyclic phenol sulfide described above can be produced by a process comprising reacting a phenol which is unsubstituted or substituted with a hydrocarbon group at the 4-position with a specific amount of elemental sulfur in the presence of a specific amount of at least one metal reagent selected from alkali metal reagents and alkaline-earth metal reagents. It has also been found that derivatives of the cyclic phenol sulfide can be produced. The present invention has been completed based on these findings.

That is, these and other objects of the present invention have been attained by a cyclic phenol sulfide represented by the following formula (1):

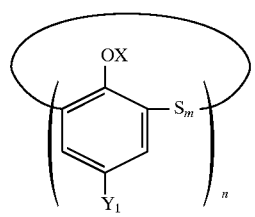

(1)

wherein X represents a hydrogen atom, a hydrocarbon group, or an acyl group; $Y_1$ represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$ (—O—$SO_2$—$OR^6$), or —$SO_3R^7$, in which $R^1$, $R^2$, $R^3$, $R^4$, $R^5$, $R^6$, and $R^7$ each represents a hydrogen atom or a hydrocarbon group; n is an integer of 3 or more; and m is an integer of 1 to 7, provided that the plural m's of the $S_m$'s are the same or different; the plural X's are the same or different; and the plural $Y_1$'s are the same or different.

Furthermore, these and other objects of the present invention have been attained by a process for producing a cyclic phenol sulfide represented by the following formula (3):

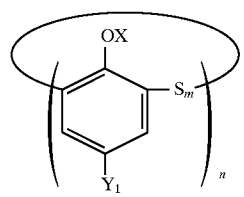

(3)

wherein $Y_2$ represents a hydrogen atom or a hydrocarbon group; n is an integer of 3 or more; and m is an integer of 1 to 7, provided that the plural m's of the $S_m$'s are the same or different; and the plural $Y_2$'s are the same or different, which comprises a step of reacting a phenol represented by the following formula (2) with at least 0.1 gram equivalent of elemental sulfur in the presence of at least 0.005 gram equivalent of at least one metal reagent selected from the group consisting of alkali metal reagents and alkaline-earth metal reagents, each per gram equivalent of the phenol represented by formula (2):

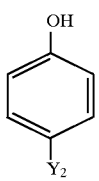

(2)

DETAILED DESCRIPTION OF THE INVENTION

In formula (1), X represents a hydrogen atom, a hydrocarbon group, or an acyl group.

The carbon atom number of the hydrocarbon group represented by X is not particularly limited as long as the number is 1 or more. Preferably, the carbon atom number of the hydrocarbon group is from 1 to 50. Examples of the hydrocarbon group include a saturated aliphatic hydrocarbon group, an unsaturated aliphatic hydrocarbon group, an alicyclic hydrocarbon group, an alicyclic-aliphatic hydrocarbon group, an aromatic hydrocarbon group, and an aromatic-aliphatic hydrocarbon group.

Preferred examples of the saturated aliphatic hydrocarbon group include an alkyl group such as methyl, ethyl, n-propyl, isopropyl, n-butyl, isobutyl, tert-butyl, n-pentyl, isopentyl, neopentyl, tert-pentyl, 2-methylbutyl, n-hexyl, isohexyl, 3-methylpentyl, ethylbutyl, n-heptyl, 2-methylhexyl, n-octyl, isooctyl, tert-octyl, 2-ethylhexyl, 3-methylheptyl, n-nonyl, isononyl, 1-methyloctyl, ethylheptyl, n-decyl, 1-methylnonyl, n-undecyl, 1,1-dimethylnonyl, n-dodecyl, n-tetradecyl, n-heptadecyl, and n-octadecyl; and a hydrocarbon group derived from a polymer or copolymer of an alkene such as ethylene, propylene, and butylene.

Preferred examples of the unsaturated aliphatic hydrocarbon group include alkenyl and alkynyl groups such as vinyl, allyl, isopropenyl, 2-butenyl, 2-methylallyl, 1,1-dimethylallyl, 3-methyl-2-butenyl, 3-methyl-3-butenyl, 4-pentenyl, hexenyl, octenyl, nonenyl, decenyl; and a hydrocarbon group derived from a polymer or copolymer of an alkyne such as acetylene, butadiene, and isoprene.

Preferred examples of the alicyclic hydrocarbon group include cycloalkyl, cycloalkenyl, and cycloalkynyl groups such as cyclopropyl, cyclobutyl, cyclopentyl, cyclohexyl, cycloheptyl, cyclooctyl, 3-methylcyclohexyl, 4-methylcyclohexyl, 4-ethylcyclohexyl, 2-methylcyclooctyl, cyclopropenyl, cyclobutenyl, cyclopentenyl, cyclohexenyl, cycloheptenyl, cyclooctenyl, 4-methylcyclohexenyl, and 4-ethylcyclohexenyl.

Preferred examples of the alicyclic-aliphatic hydrocarbon group include cycloalkyl-, cycloalkenyl-, or cycloalkynyl-substituted alkyl, alkenyl, and alkynyl groups such as cyclopropylethyl, cyclobutylethyl, cyclopentylethyl, cyclohexylmethyl, cyclohexylethyl, cycloheptylmethyl, cyclooctylethyl, 3-methylcyclohexylpropyl, 4-methylcyclohexylethyl, 4-ethylcyclohexylethyl, 2-methylcyclooctylethyl, cyclopropenylbutyl, cyclobutenylethyl, cyclopentenylethyl, cyclohexenylmethyl, cycloheptenylmethyl, cyclooctenylethyl, 4-methylcyclohexenylpropyl, and 4-ethylcyclohexenylpentyl.

Preferred examples of the aromatic hydrocarbon group include an aryl group such as phenyl and naphthyl; and alkylaryl, alkenylaryl, and alkynylaryl groups such as 4-methylphenyl, 3,4-dimethylphenyl, 3,4,5-trimethylphenyl, 2-ethylphenyl, n-butylphenyl, tert-butylphenyl, amylphenyl, hexylphenyl, nonylphenyl, 2-tert-butyl-5-methylphenyl, cyclohexylphenyl, cresyl, oxyethylcresyl, 2-methoxy-4-tert-butylphenyl, and dodecylphenyl. The alkyl moiety of the alkylaryl group, the alkenyl moiety of the alkenylaryl group, and the alkynyl moiety of the alkynylaryl group may have a cyclic structure.

Preferred examples of the aromatic-aliphatic hydrocarbon group include aralkyl, aralkenyl, and aralkynyl groups such as benzyl, 1-phenylethyl, 2-phenylethyl, 2-phenylpropyl, 3-phenylpropyl, 4-phenylbutyl, 5-phenylpentyl, 6-phenylhexyl, 1-(4-methylphenyl)ethyl, 2-(4-methylphenyl)ethyl, 2-methylbenzyl, and 1,1-dimethyl-2-phenylethyl. The alkyl moiety of the aralkyl group, the alkenyl moiety of the aralkenyl group, and the alkynyl moiety of the aralkynyl group may have a cyclic structure.

These hydrocarbon groups may be further substituted with at least one of the hydrocarbon groups represented by X.

The carbon atom number of the acyl group represented by X is not particularly limited as long as the number is 1 or more. Preferably, the carbon atom number of the acyl group is from 1 to 40. Preferred examples of the acyl group include formyl, acetyl, propionyl, butyryl, isobutyryl, valeryl, isovaleryl, oxalyl, succinyl, pivaloyl, stearoyl, benzoyl, phenylpropionyl, toluoyl, naphthoyl, phthaloyl, indancarbonyl, p-methylbenzoyl, and cyclohexylcarbonyl.

In formula (1), $Y_1$ represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$.

Examples of the hydrocarbon group and the —$COR^1$ group both represented by $Y_1$ include the same hydrocarbon groups and acyl groups as those enumerated hereinabove with regard to X. Preferred examples thereof also include the same preferred groups.

Examples of the halogenated hydrocarbon group include halogenated hydrocarbon groups formed by halogen-substituting the same hydrocarbon groups as those enumerated hereinabove with regard to X. Preferred examples thereof also include halogenated hydrocarbon groups derived from the same preferred hydrocarbon groups. Examples of the halogen include fluorine, chlorine, bromine, and iodine atoms. The halogenated hydrocarbon atoms may be substituted with two or more halogens, and the substituted halogens may be the same or different.

Examples of the halogen atom represented by $Y_1$ include fluorine, chlorine, bromine, and iodine atoms.

$R^1$, $R^2$, $R^3$, $R^4$, $R^5$, $R^6$, and $R^7$ each represents a hydrogen atom or a hydrocarbon group. Examples of the hydrocarbon group include the same hydrocarbon groups as those enumerated hereinabove with regard to X, and preferred examples thereof also include the same preferred groups.

The above hydrocarbon group may be substituted with at least one substituent such as —$COR^1$, —$OR^2$, —$COOR^3$, —CN, —$CONH_2$, —$NO_2$, —$NR^4R^5$, a halogen atom, —$SO_4R^6$, or —$SO_3R^7$. The halogen atom may be any of fluorine, chlorine, bromine, and iodine atoms. These substituents may be of one kind or two or more kinds. The number of the substituents may be one or more per hydrocarbon group.

m is an integer of from 1 to 7, preferably from 1 to 5, and more preferably from 1 to 3.

n is an integer of 3 or more, preferably 4 or more, and more preferably 5 or more. Although there is no particular upper limit on the value of n, n is preferably 16 or less, and more preferably 12 or less.

In formula (1), there are three or more X's per molecule. The plural X's may be the same or different.

Further, in formula (1), there are three or more $Y_1$'s per molecule. The plural $Y_1$'s may be the same or different.

A process for producing the cyclic phenol sulfide of the present invention is then explained.

The cyclic phenol sulfide of the present invention can be produced by reacting a phenol represented by formula (2) with at least 0.1 gram equivalent of elemental sulfur per gram equivalent of the phenol in the presence of at least 0.005 gram equivalent, per gram equivalent of the phenol, of at least one metal reagent selected from the group consisting of alkali metal reagents and alkaline-earth metal reagents.

In formula (2), $Y_2$ represents a hydrogen atom or a hydrocarbon group. This hydrocarbon group is the same as the hydrocarbon group described hereinabove with regard to X in formula (1), except that the especially preferred range of the number of carbon atoms contained therein is from 1 to 18.

The phenols may be used either alone or in combination of two or more thereof.

The phenol and elemental sulfur are introduced as starting materials in such a proportion that the amount of the elemental sulfur is at least 0.1 gram equivalent, preferably at least 0.35 gram equivalent, per gram equivalent of the phenol represented by formula (2). Although there is no particular upper limit on the amount of the elemental sulfur introduced as a starting material, the amount thereof is preferably 20 gram equivalent or less, more preferably 10 gram equivalent or less, per gram equivalent of the phenol represented by formula (2).

Examples of the alkali metal reagents for use in the reaction include elemental alkali metals, alkali metal hydrides, alkali metal hydroxides, alkali metal carbonates, alkali metal alkoxides, and alkali metal halides. Examples of the alkaline-earth metal reagents include elemental alkaline earth metals, alkaline-earth metal hydrides, alkaline-earth metal hydroxides, alkaline-earth metal oxides, alkaline-earth metal carbonates, alkaline-earth metal alkoxides, and alkaline-earth metal halides.

Preferred examples of the alkali metal reagents include elemental alkali metals, alkali metal hydrides, alkali metal hydroxides, alkali metal carbonates and alkali metal alkoxides. Preferred examples of the alkaline-earth metal reagents include elemental alkaline earth metals, alkaline-earth metal hydrides, alkaline-earth metal hydroxides, alkaline-earth metal oxides, alkaline-earth metal carbonates, and alkaline-earth metal alkoxides.

Specific preferred examples of the alkali metal reagents include elemental lithium metal, elemental sodium metal, elemental potassium metal, lithium hydride, sodium hydride, potassium hydride, lithium hydroxide, sodium hydroxide, potassium hydroxide, rubidium hydroxide, cesium hydroxide, lithium carbonate, sodium carbonate, potassium carbonate, rubidium carbonate, cesium carbonate, sodium butoxide, sodium ethoxide, lithium butoxide, lithium ethoxide, potassium butoxide, and potassium ethoxide.

Specific preferred examples of the alkaline-earth metal reagents include elemental calcium metal, elemental magnesium metal, calcium hydride, calcium oxide, barium oxide, magnesium oxide, strontium oxide, calcium hydroxide, barium hydroxide, magnesium hydroxide, strontium hydroxide, calcium carbonate, barium carbonate, strontium carbonate, magnesium methoxide, and magnesium ethoxide.

These metal reagents may be used alone or in combination of two or more thereof.

The use amount of the metal reagent is at least 0.005 gram equivalent, preferably at least 0.01 gram equivalent, per gram equivalent of the phenol represented by formula (2). Although there is no particular upper limitation on the use amount of the metal reagent, the amount thereof is preferably 10 gram equivalent or less, and more preferably 5 gram equivalent or less, per gram equivalent of the phenol represented by formula (2).

The reaction in this invention is preferably conducted in an inert gas atmosphere.

Examples of the inert gas include nitrogen, argon, and helium.

It is preferred in the present invention to perform the reaction while removing the water and hydrogen sulfide which generate during the reaction.

For facilitating removal of the hydrogen sulfide generating during the reaction, it is preferred to conduct the reaction in an inert gas stream.

The reaction temperature is preferably 80° C. or more, and more preferably 100° C. or more. Although there is no particular upper limit on the reaction temperature, the reaction temperature is preferably at 300° C. or less, and more preferably 280° C. or less.

Although the reaction time is not particularly limited, the reaction may be usually conducted for 1 to 24 hours.

A solvent is preferably used for this reaction, if needed. The solvent is not particularly limited. Preferred examples of the solvent include an aliphatic hydrocarbon (e.g., hexadecane), an aromatic hydrocarbon (e.g., cymen, pseudocumene), an ether (e.g., diphenyl ether, hexyl ether, triethylene glycol diethyl ether, tetraethylene glycol dimethyl ether), a sulfide (e.g., diphenyl sulfide), a dihydric alcohol (e.g, ethylene glycol, diethylene glycol), and mixtures thereof. Beside these, any other solvent can be used as long as it is harmless during the reaction and during the use of the product.

For the purpose of homogenizing a mixture of the starting materials, water may be added at the beginning of the reaction.

By hydrolyzing the reaction mixture resulting from the above-described reaction with an acidic aqueous solution, e.g., aqueous sulfuric acid solution or aqueous hydrochloric acid solution, a reaction product comprising the compound of the present invention can be obtained.

If the reaction product is a mixture of two or more cyclic phenol sulfides, the individual compounds may be separated and purified, for example, by an ordinary technique, e.g., column chromatography or recrystallization, or by a combination of such techniques.

The reaction product yielded by the process described above comprises a cyclic phenol sulfide represented by formula (3).

In formula (3), m is an integer of from 1 to 7, in most cases from 1 to 5.

n is an integer of 3 or more. Although there is no particular upper limit on the value of n, n is in most cases 16 or less, especially 12 or less.

In formula (3), $Y_2$ is the same as that in formula (2).

In formula (3), there are three or more $Y_2$'s per molecule. These plural $Y_2$'s may be the same or different.

Further, in formula (3), there are three or more $S_m$'s per molecule. The plural m's of these $S_m$'s may be the same or different.

The hydrogen atom of each phenolic hydroxyl group in the thus-yielded cyclic phenol sulfide may be converted to X in formula (1).

For this conversion, a method in which an acylating agent, e.g., acetyl chloride or acetic anhydride, is used to convert the hydrogen atom of each phenolic hydroxyl group in the cyclic phenol sulfide into an acyl group may be used.

Also usable is a method in which the hydrogen atom of each phenolic hydroxyl group in the cyclic phenol sulfide is replace with an alkali metal and this compound reacts a halogenated hydrocarbon by the Williamson reaction to convert the alkali metal into a hydrocarbon group.

The substituent $Y_2$ of the yielded cyclic phenol sulfide may be converted to another substituent such as, e.g., any of the substituents represented by $Y_1$ in formula (1).

For converting $Y_2$ into another substituent, a method in which a cyclic phenol sulfide represented by formula (3) wherein $Y_2$ is an alkyl group is dealkylated with a catalyst, e.g., aluminum chloride or cobalt oxide, to convert each $Y_2$ into a hydrogen atom may be used.

In another method for converting $Y_2$ into still another substituent, the dealkylated cyclic phenol sulfide reacts with an appropriate nitrating agent, e.g., nitronium tetrafluoroborate or nitric acid, to convert each $Y_2$-derived hydrogen atom into a nitro group.

The nitro group can be converted to an amino group by reduction with an appropriate reducing agent, e.g., iron/hydrochloric acid. It is also possible to diazotize the aminated compound with, e.g., sodium nitrite and react the diazotized compound with an appropriate halogenating agent, e.g., copper chloride in the presence of hydrochloric acid, a cyano-introducing agent, or water to thereby convert each amino group into a halogen group, a cyano group, or a hydroxyl group, respectively.

The hydroxyl group can be converted to an acidic sulfate group by the action of a sulfating agent, e.g., sulfuric acid.

The hydroxyl group can also be converted to an alkyl ether by converting the hydroxylated compound into an alkali metal phenoxide, e.g., sodium phenoxide, and reacting this phenoxide with an alkyl halide.

Each $Y_2$-derived hydrogen atom of the dealkylated cyclic phenol sulfide can be converted to a sulfo group by reacting the dealkylated phenol sulfide with fuming sulfuric acid.

Further, each $Y_2$-derived hydrogen atom of the dealkylated cyclic phenol sulfide can be converted to an acyl group by reacting the dealkylated phenol sulfide with an acid halide if necessary in the presence of a catalyst, e.g., a Lewis acid.

Other methods for converting $Y_2$ into another substituent include a method in which the cyclic phenol sulfide is oxidized with an appropriate oxidizing agent, e.g., permanganate, to convert each $Y_2$ into a carboxyl group. The carboxyl group can be converted to an ester group by reaction with an alcohol. The carboxyl group can be also converted to an amide group by reaction with an amine.

The cyclic phenol sulfide of the present invention is an absolutely novel compound having a cyclic structure comprising phenol structures bonded to each other through sulfur atoms. This compound is useful as, e.g., an antioxidant, catalyst, metal-trapping agent, light sensor, ion sensor, sensor with substrate specificity, separating-membrane material, polymer material, phase-transfer catalyst, synthetic enzyme, light energy converter, or an intermediate for functional molecules using a recognition ability of an ion or molecule.

The present invention is now illustrated in greater detail by way of the following examples, but it should be understood that the present invention is not to be construed as being limited thereto. Unless otherwise indicated herein, all parts, percents, ratios and the like are by weight.

EXAMPLES

Example 1

To 45.2 g of 4-tert-butylphenol were added 14.4 g of elemental sulfur and 3.0 g of sodium hydroxide. This mixture was gradually heated to 230° C. with stirring in a nitrogen steam over a period of 4 hours, and stirring was then further continued for 2 hours. During this reaction, the water and hydrogen sulfide generated by the reaction were removed. The water distilled off during the reaction amounted to about 0.8 g, and the hydrogen sulfide generated by the reaction amounted to about 6 g. The color of the resulting reaction mixture was an extremely dark red (5R 2/2.5, according to JIS Z 8102). After this reaction mixture was cooled to room temperature, 500 ml of ether was added. The reaction mixture was then sufficiently hydrolyzed with 1N sulfuric acid. The ether layer was taken out by separation, and the ether was distilled off therefrom. Mass spectrometric analysis of the residue revealed that the reaction had yielded a mixture of cyclic phenol sulfides which consisted mainly of the cyclic phenol sulfide represented by formula (3) wherein n=4, m=1, and $Y_2$=tert-butyl and further contained cyclic phenol sulfides which varied in n from 3 to 15. This reaction mixture was separated into individual compounds by silica gel column chromatography (hexane/chloroform) to obtain a crude reaction product, which was then recrystallized from chloroform/acetone. As a result, 4.32 g of the cyclic phenol sulfide represented by formula (3) wherein n=4, m=1, and $Y_2$=tert-butyl was isolated. The yield of this isolated compound based on the tert-butylphenol was 11%.

The reaction product, which was isolated as colorless transparent crystals, was 5, 11, 17, 23-tetra-tert-butyl-25, 26, 27, 28-tetrahydroxy-2, 8, 14, 20-tetrathia-[$19.3.1.1^{3,7}1^{9,13}1^{15,19}$]octacosa-1(25), 3, 5, 7(28), 9, 11, 13(27), 15, 17, 19(26), 21, 23-dodecaene (I).

Analytical data for reaction product (I) are given below.

Melting point: 320°–322° C.

IR (KRS-5): 3324 (OH stretching), 2962 (CH stretching) $cm^{-1}$ $^1$H NMR (CDCl$_3$) δ: 9.60 (s, 1, OH), 7.64 (s, 2, ArH), 1.22 (S, 9, C(CH$_3$)$_3$) ppm $^{13}$C NMR (CDCl$_3$) δ:155.6, 144.7, 136.4, 120.5 (Ar), 34.2 ($\underline{C}$(CH$_3$)$_3$), 31.3 (C($\underline{C}$H$_3$)$_3$) ppm MS m/z: 720 (M$^+$)

Elemental analysis, % Calculated for $C_{40}H_{48}O_4S_4$: C, 66.62; H, 6.71; S, 17.79 Found: C, 66.37; H, 6.57; S, 17.22

Example 2

A mixture of 64.5 g of 4-tert-butylphenol, 27.5 g of elemental sulfur, and 17.2 g of sodium hydroxide was allowed to react in the same manner as in Example 1, except that 19 ml of tetraethylene glycol dimethyl ether was used. The resulting reaction mixture was subjected to hydrolysis, extraction with ether, and then separation by a combination of column chromatography (hexane/chloroform) and recrystallization from chloroform/acetone in the same manner as in Example 1. As a result, 37.9 g of the cyclic phenol sulfide represented by formula (3) wherein n=4, m=1, and $Y_2$=tert-butyl (the same as reaction product (I)) was isolated. The yield of this isolated compound based on the tert-butylphenol was 49%.

Example 3

Reaction was carried out in the same manner as in Example 1, except that in place of sodium hydroxide, barium hydroxide was used in a reactant mixture consisting of 52.3 g of 4-tert-butylphenol, 22.3 g of elemental sulfur, and 27.6 g of barium hydroxide (octahydrate). The resulting reaction mixture was subjected to hydrolysis, extraction with ether, and then separation and purification by a combination of column chromatography (ether/chloroform) and recrystallization from chloroform/acetone in the same manner as in Example 1. As a result, 3.04 g of the cyclic phenol sulfide represented by formula (3) wherein n=5, m=1, and $Y_2$=tert-butyl, that is, 5, 11, 17, 23, 29-penta-tert-butyl-31, 32, 33, 34, 35-pentahydroxy-2, 8, 14, 20, 26-pentathia [$25.3.1.1^{3,7}1^{9,13}1^{15,19}1^{21,25}$]-pentatriaconta-1(31), 3, 5, 7(35), 9, 11, 13(24), 15, 17, 19(33), 21, 23, 25(32), 27, 29-pentadecaene (III), was isolated. The yield of this isolated compound (III) based on the tert-butylphenol was 5%.

Analytical data for reaction product (III) are given below.

$^1$H NMR (CDCl$_3$) δ: 7.47 (s, 2, ArH), 1.21 (s, 9, C(CH$_3$)$_3$) ppm $^{13}$C NMR (CDCl$_3$) δ: 154.3, 144.1, 133.6, 119.6 (Ar), 34.2 ($\underline{C}$(CH$_3$)$_3$), 31.3 (C($\underline{C}$H$_3$)$_3$) ppm MS m/z: 900 (M$^+$)

Elemental analysis, % Calculated for C$_{50}$H$_{60}$O$_5$S$_5$: C, 66.62; H, 6.71; S, 17.79 Found: C, 66.34; H, 6.61; S, 17.04

Example 4

Reaction was carried out in the same manner as in Example 3, except that the reaction time was changed to 8 hours. The resulting reaction mixture was subjected to silica gel column chromatography (hexane/chloroform) to obtain a crude reaction product, which was then recrystallized from chloroform/acetone. As a result, 1.09 g of 5, 11, 17, 23, 29, 35-hexa-tert-butyl-37, 38, 39, 40, 41, 42-hexahydroxy-2, 8, 14, 20, 26, 32-hexathia[31.3.1.1$^{3,7}$1$^{9,13}$1$^{15,19}$1$^{21,25}$1$^{27,31}$]dotetraconta-1(37), 3, 5, 7(42), 9, 11, 13(41), 15, 17, 19(40), 21, 23, 25(39), 27, 29, 31(38), 33, 35-octadecaene (IV) was obtained as a white powder.

Reaction product (IV) is the cyclic phenol sulfide represented by formula (3) wherein m=1, n=6, and Y$_1$=tert-butyl.

Analytical data for reaction product (IV) are given below.

$^1$H NMR (CDCl$_3$) δ: 9.18 (s, 1, OH), 7.59 (s, 2, ArH), 1.23 (s, 9, C(CH$_3$)$_3$) ppm $^{13}$C NMR (CDCl$_3$) δ: 155.3, 144.4, 135.4, 120.4 (Ar), 34.2 ($\underline{C}$(CH$_3$)$_3$), 31.3 (C($\underline{C}$H$_3$)$_3$) ppm MS m/z: 1080 (M$^+$)

Elemental analysis, % Calculated for C$_{60}$H$_{72}$O$_6$S$_6$: C, 66.62; H, 6.71; S, 17.79 Found: C, 66.20; H, 6.57; S, 17.12

Example 5

To 47.7 g of 4-tert-octylphenol (purity, 95%) were added 10.6 g of elemental sulfur and 4.4 g of sodium hydroxide. This suspension was stirred at 130° C. in a nitrogen stream to react the reactants for 2 hours.

The color of the reaction mixture after the above reaction was a dark red (5R 2.5/9). This mixture was heated to 170° C. and reacted at this temperature for 2 hours, and was then heated to 250° C. and reacted at this temperature for 3 hours and 30 minutes. During this reaction, the water and hydrogen sulfide generated by the reaction were removed. The color of the resulting reaction mixture was an extremely dark red (5R 2/2.5). The water distilled off during the reaction amounted to about 1.5 g, and the hydrogen sulfide generated by the reaction amounted to about 5 g. Ether was added to the reaction mixture. The ether was distilled off from the ether layer. Mass spectrometric analysis of the residue revealed that the reaction had yielded a mixture of cyclic phenol sulfides which consisted mainly of the cyclic phenol sulfide represented by formula (3) wherein n=4, m=1, and Y$_2$=tert-octyl and further contained cyclic phenol sulfides which varied in n from 3 to 7. This reaction mixture was separated into individual compounds by silica gel column chromatography (hexane/chloroform) to obtain a crude reaction product, which was then recrystallized from chloroform/acetone. As a result, 2.98 g of the cyclic phenol sulfide represented by formula (3) wherein n=4, m=1, and Y$_2$=tert-octyl, that is, 25, 26, 27, 28-tetrahydroxy-5, 11, 17, 23-tetra-tert-octyl-2, 8, 14, 20-tetrathia[19.3.1.1$^{3,7}$1$^{9,13}$15, 19]octacosa-1(25), 3, 5, 7(28),9, 11 13(27), 15, 17, 19(26), 21, 23-dodecaene (V), was isolated. The yield of this isolated compound (V) based on the tert-octylphenol was 8%.

Analytical data for reaction product (V) are given below.

Melting point: 243°–245° C.

IR (KRS-5): 3290 (OH stretching), 2954 (CH stretching) cm$^{-1}$ $^1$H NMR (CDCl$_3$) δ: 9.20 (s, 1, OH), 7.57 (s, 2, ArH), 1.59 (s, 2, CH$_2$), 1.24 (s, 6, CH$_3$), 0.56 (s, 9, C(CH$_3$)$_3$) ppm $^{13}$C NMR (CDCl$_3$) δ155.1, 143.4, 136.6, 120.4 (Ar), 57.0 (CH$_2$), 38.0 (Ar—C), 32.3 ($\underline{C}$(CH$_3$)$_3$), 31.7 (C($\underline{C}$H$_3$)$_3$), 31.2 (Ar—C(CH$_3$)$_2$) ppm MS m/z: 944 (M$^+$)

Elemental analysis, % Calculated for C$_{56}$H$_{80}$O$_4$S$_4$: C, 71.14; H, 8.53; S, 13.57 Found: C, 70.74; H, 8.34; S, 13.10

Example 6

In 120 ml of acetic anhydride was suspended 5 g of the 5, 11, 17, 23-tetra-tert-butyl-25, 26, 27, 28-tetrahydroxy-2, 8, 14, 20-tetrathia[19.3.1.1$^{3,7}$1$^{9,13}$1$^{15,19}$]octacosa-1(25), 3, 5, 7(28), 9, 11, 13(27), 15, 17, 19(26), 21, 23-dodecaene obtained in Example 1. Two drops of concentrated sulfuric acid were added thereto, and this suspension was maintained with refluxing for 24 hours. One liter of water was then added thereto, and this mixture was filtered. The filtration residue was washed with water and then dissolved in acetone. This solution was filtered to remove the insoluble matter, and the acetone was distilled off from the filtrate. As a result, 4.2 g of 25, 26, 27, 28-tetraacetoxy-5, 11, 17, 23-tetra-tert-butyl-2, 8, 14, 20-tetrathia[19.3.1.1$^{3,7}$1$^{9,13}$1$^{15,}$ $_{19}$]octacosa-1(25), 3, 5, 7(28), 9, 11, 13(27), 15, 17, 19(26), 21, 23-dodecaene (VI) was obtained as a white powder.

Reaction product (VI) is the cyclic phenol sulfide represented by formula (1) wherein m=1, n=4, X=acetyl, and Y$_1$=tert-butyl.

Analytical data for reaction product (VI) are given below.

IR (KRS-5): 2964 (CH stretching), 1769 (C═O stretching) cm$^{-1}$ $^1$H NMR (CDCl$_3$) δ: 7.45 (s, 2, ArH), 1.58 (s, 3, CH$_3$CO$_2$—), 1.29 (s, 9, C(CH$_3$)$_3$) ppm $^{13}$C NMR (CDCl$_3$) δ: 166.0 (C═O), 149.6, 149.2, 128.5, 128.3 (Ar), 34.8 ($\underline{C}$(CH$_3$)$_3$), 31.3 (C($\underline{C}$H$_3$)$_3$), 19.6 ($\underline{C}$H$_3$CO$_2$—) ppm MS m/z: 888 (M$^+$)

Elemental analysis, % Calculated for C$_{48}$H$_{56}$O$_8$S$_4$: C, 64.83; H, 6.35; S, 14.42 Found: C, 64.35; H, 6.22; S, 13.95

Example 7

NaH (0.5 g, 60% in mineral oil) was washed with anhydrous n-hexane, before 5 ml of anhydrous DMF was added thereto. This mixture was stirred. Thereto was added dropwise a solution in 50 ml anhydrous toluene of 1.0 g of 5, 11, 17, 23-tetra-tert-butyl-25, 26, 27, 28-tetrahydroxy-2, 8, 14, 20-tetrathia[19.3.1.1$^{3,7}$1$^{9,13}$1$^{15,19}$]octacosa-1(25), 3, 5, 7(28), 9, 11, 13(27), 15, 17, 19(26), 21, 23-dodecaene (I) obtained in Example 1. After the resulting mixture was stirred at room temperature for 2 hours, 5 ml of methyl iodide was added. This mixture was further stirred at room temperature for 2 hours, subsequently at 60° C. for 30 minutes, and then at 80° C. for 1 hour, before being heated at 120° C. with refluxing for 2 hours. After cooling, 50 ml of 1N hydrochloric acid was added to the reaction mixture, following which extraction with toluene was conducted. The extract was washed with 10% aqueous sodium thiosulfate solution and then with distilled water. The solvent was distilled off to obtain 1.30 g of a residue, which was washed with methanol and then with acetone. The residue was dissolved in chloroform, and the insoluble matter was removed by filtration. The solvent was then distilled off to obtain 1.13 g of white crystals. This crude reaction product was dissolved in 6 ml of chloroform, and 50 ml of acetone was added thereto to cause crystallization. This mixture was filtered to obtain 0.83 g of crystals. A 0.73 g portion of these crystals was recrystallized from chloroform to obtain 0.53 g of the desired compound, i.e., 5, 11, 17, 23-tetra-tert-butyl-25, 26, 27, 28-tetramethoxy-2, 8, 14, 20-tetrathia[19.3.1.1$^{3,7}$1$^{9,13}$1$^{15,19}$]octacosa-1(25), 3, 5, 7(28), 9, 11, 13(27), 15, 17, 19(26), 21, 23-dodecaene (VII).

Reaction product (VII) is the cyclic phenol sulfide represented by formula (1) wherein m=1, n=4, X=methyl, and Y$_1$=tert-butyl. This reaction product had the following properties.

Colorless transparent crystals

Melting point: 295°–298° C.

MS m/z: 776 (M$^+$)

$^1$H NMR (CDCl$_3$) δ:7.44 (s, 2, ArH), 3.45 (s, 3, OCH$_3$), 1.24 (s, 9, C(CH$_3$)$_3$) ppm $^{13}$C NMR (CDCl$_3$) δ: 158.5, 145.9, 131.3, 129.1 (Ar), 59.0 (O$\underline{C}$H$_3$), 34.1 ($\underline{C}$(CH$_3$)$_3$), 31.2 (C($\underline{C}$H$_3$)$_3$) ppm IR (KBr) υ: 2962 (CH stretching), 1579, 1543 (aromatic-CC stretching) cm$^{-1}$ Elemental analysis, % Calculated for C$_{44}$H$_{56}$O$_4$S$_4$: C, 68.00; H, 7.26; S, 16.50 Found: C, 67.97; H, 7.24; S, 16.35

Example 8

To 200 ml of toluene were added 3.84 g of 5, 11, 17, 23-tetra-tert-butyl-25, 26, 27, 28-tetrahydroxy-2, 8, 14, 20-tetrathia[19.3.1.1$^{3,7}$1$^{9,13}$1$^{15,19}$]octacosa-1(25), 3, 5, 7(28), 9, 11, 13(27), 15, 17, 19(26), 21, 23-dodecaene (I) obtained in Example 1 and 1.0 g of aluminum chloride. This solution was heated at 55° C. for 24 hours to react the reactants. This reaction mixture was treated with 120 ml of 1N hydrochloric acid and then extracted with toluene. It was ascertained through FD-MS spectrometry that the reaction product was a mixture of four compounds formed from compound (I) by eliminating one, two, three, and four, respectively, of the four butyl groups thereof. This solution was mixed with a large quantity of ether to cause crystallization, and the resulting crystals were taken out by filtration and recrystallized from toluene. The solvent was then removed at a reduced pressure to obtain 0.05 g of the desired compound, i.e., 25, 26, 27, 28-tetrahydroxy-2, 8, 14, 20-tetrathia-[19.3.1.1$^{3,7}$1$^{9,13}$1$^{15,19}$]octacosa-1(25), 3, 5, 7(28), 9, 11, 13(27), 15, 17, 19(26), 21, 23-dodecaene (VIII).

Reaction product (VIII) is the cyclic phenol sulfide represented by formula (1) wherein m=1, n=4, X=H, and Y$_1$=H. This reaction product had the following properties.

White crystals

MS m/z: 496 (M$^+$)

$^1$H NMR (CDCl$_3$) δ: 9.45 (s, 1, OH), 7.61 (d, 2, J=8 Hz, ArH), 6.75 (t, 1, J=8 Hz, ArH) ppm $^{13}$C NMR (CDCl$_3$) δ: 157.9, 139.3, 121.7, 120.9 (Ar) ppm Elemental analysis, % Calculated for C$_{24}$H$_{16}$O$_4$S$_4$: C, 58.04; H, 3.25; S, 25.83 Found: C, 58.60; H, 3.40; S, 24.97

Example 9

In 250 ml of chloroform was dissolved 1.49 g of 25, 26, 27, 28-tetrahydroxy-2, 8, 14, 20-tetrathia[19.3.1.1$^{3,7}$1$^{9,}$ $_{13}$1$^{15,19}$]-octacosa-1(25), 3, 5, 7(28), 9, 11, 13(27), 15, 17, 19(26), 21, 23-dodecaene (VIII) obtained in Example 8. To this solution was added 4.86 g of NBS (N-bromosuccinimide). This solution was stirred at room temperature for 10 hours, and then allowed to stand for 62 hours. This reaction mixture was treated with 5% NaHSO$_3$. The resulting precipitate was taken out by filtration to obtain 1.62 g of crystals. A 1.23 g portion of these crystals was dissolved in 250 ml of chloroform and 0.68 g of NBS was added, following which the same procedure for reaction and separation was carried out. As a result, 0.28 g of the desired compound, i.e., 5, 11, 17, 23-tetrabromo-25, 26, 27, 28-tetrahydroxy-2, 8, 14, 20-tetrathia[19.3.1.1$^{3,7}$1$^{9,13}$1$^{15,19}$]-octacosa-1(25), 3, 5, 7(28), 9, 11, 13(27), 15, 17, 19(26), 21, 23-dodecaene (IX), was obtained.

This reaction product is the cyclic phenol sulfide represented by formula (1) wherein m=1, n=4, X=H, and Y$_1$=Br. This reaction product had the following properties.

Orange crystals

MS m/z: 808 (M$^+$), 810 (M$^+$+2), 812 (M$^+$+4), 814 (M$^+$+6), 816 (M$^+$+8)

$^1$H NMR (CDCl$_3$) δ:7.77 (s, ArH) ppm

Elemental analysis, % Calculated for C$_{24}$H$_{12}$Br$_4$O$_4$S$_4$: C, 35.49; H, 1.49; Br, 39.35; S, 15.79 Found: C, 35.39; H, 1.46; Br, 39.28; S, 15.69

Example 10

To 20 ml of nitrobenzene were added 0.49 g of 25, 26, 27, 28-tetrahydroxy-2, 8, 14, 20-tetrathia[19.3.1.1$^{3,7}$1$^{9,13}$1$^{15,19}$]octacosa-1(25), 3, 5, 7(28), 9, 11, 13(27), 15, 17, 19(26), 21, 23-dodecaene (VIII) obtained in Example 8 and 1.33 g of aluminum chloride. To this solution was added dropwise 1.41 g of benzoyl chloride over a period of about 5 minutes. This reaction mixture was stirred at room temperature for 24 hours, and then treated with an aqueous solution prepared by diluting 1 ml of 36% hydrochloric acid with 20 ml of distilled water. Thereto was added 150 ml of ether, and the crystals precipitated were removed by filtration. The filtrate was extracted with ether, and the solvent was removed at a reduced pressure to obtain 0.83 g of the desired compound, i.e., 5, 11, 17, 23-tetrabenzoyl-25, 26, 27, 28-tetrahydroxy-2, 8, 14, 20-tetrathia[19.3.1.1$^{3,7}$1$^{9,13}$1$^{15,19}$]octacosa-1(25), 3, 5, 7(28), 9, 11, 13(27), 15, 17, 19(26), 21, 23-dodecaene (X).

This reaction product is the cyclic phenol sulfide represented by formula (1) wherein m=1, n=4, X=H, and Y$_1$=benzoyl. This reaction product had the following properties.

White crystals

MS m/z: 912 (M$^+$)

Elemental analysis, % Calculated for C$_{52}$H$_{32}$O$_8$S$_4$: C, 68.40; H, 3.53; S, 14.05 Found: C, 68.32; H, 3.51; S, 13.96

Example 11

To 0.78 g of 25, 26, 27, 28-tetrahydroxy-2, 8, 14, 20-tetrathia[19.3.1.1$^{3,7}$1$^{9,13}$1$^{15,19}$]octacosa-1(25), 3, 5, 7(28),9, 11, 13(27), 15, 17, 19(26), 21, 23-dodecaene (VIII) obtained in Example 8 was added 10 ml of concentrated sulfuric acid. The reactants were reacted at 80° C. for 4 hours to conduct sulfonation first. The resulting reaction mixture was then allowed to cool, and 18 ml of water was added. Subsequently, 1.0 ml of 60% nitric acid was added thereto dropwise with cooling with ice water. After completion of the addition, the reaction mixture was continuously stirred at room temperature for 12 hours. The resulting precipitate was taken out by filtration, sufficiently washed with water, and then dried. As a result, 0.10 g of the desired compound, i.e., 25, 26, 27, 28-tetrahydroxy-5, 11, 17, 23-tetranitro-2, 8, 14, 20-tetrathia-[19.3.1.1$^{3,7}$1$^{9,13}$1$^{15,19}$] octacosa-1(25), 3, 5, 7(28), 9, 11, 13(27), 15, 17, 19(26), 21, 23-dodecaene (XI), was obtained.

Reaction product (XI) is the cyclic phenol sulfide represented by formula (1) wherein m=1, n=4, X=H, and Y$_1$=nitro. This reaction product had the following properties.

White powder

MS m/z: 676 (M$^+$)

$^1$H NMR (M$_2$SO-d6) δ: 8.43 (s, ArH) ppm

Elemental analysis, % Calculated for $C_{24}H_{12}N_4O_{12}S_4$: C, 42.60; H, 1.79; N, 8.28; S, 18.96 Found: C, 42.51; H, 1.76; N, 8.23; S, 18.88

Example 12

In 31.7 ml of diphenyl ether was dissolved 48.1 g of 4-phenylphenol. To this solution were added 25.6 g of elemental sulfur and 8 g of sodium hydroxide. In a nitrogen stream, this mixture was gradually heated to 230° C. with stirring over a period of 4 hours and then continuously stirred for further 2 hours, while removing the water and hydrogen sulfide generated by the reaction. After this reaction mixture was cooled to room temperature, it was diluted with ether and neutralized with 1N sulfuric acid. The resulting precipitate was recrystallized from dioxane and then from chloroform/ether. As a result, 15.53 g of 25, 26, 27, 28-tetrahydroxy-5, 11, 17, 23-tetraphenyl-2, 8, 14, 20-tetrathia[19.3.1.1$^{3,7}$1$^{9,13}$1$^{15,19}$]octacosa-1(25), 3, 5, 7(28), 9, 11, 13(27), 15, 17, 19(26), 21, 23-dodecaene (XII) was obtained.

This reaction product is the cyclic phenol sulfide represented by formula (1) wherein m=1, n=4, X=H, and Y$_1$=phenyl. This reaction product had the following properties.

White powder $^1$H NMR (CDCl$_3$) δ: 9.66 (s, 1, OH), 7.89 (s, 2, ArH), 7.43 (d, 2, J=8 Hz, PhH), 7.39 (t, 2, J=8 Hz, PhH), 7.31 (t, 1, J=8 Hz, PhH) ppm $^{13}$C NMR (CDCl$_3$) δ: 157.2, 138.9, 137.9, 135.4, 128.9, 127.5, 126.8, 121.2 (Ar) ppm MS m/z: 800 (M$^+$)

Elemental analysis, % Calculated for $C_{48}H_{32}O_4S_4$: C, 71.97; H, 4.03; S, 16.01 Found: C, 71.87; H, 4.00; S, 15.92

Example 13

Reaction was carried out in the same manner as in Example 1, except that lithium hydroxide was used in place of sodium hydroxide and 50 ml of tetraethylene glycol dimethyl ether and tetradecane was used as a mixed solvent in a reactant mixture consisting of 90.3 g of 4-tert-butylphenol, 57.6 g of elemental sulfur, and 3.85 g of lithium hydroxide (monohydrate). The resulting reaction mixture was subjected to hydrolysis, and extraction with ether. After the ether was distilled off, the reaction mixture was dissolved in chloroform, and then subjected to column chromatography (hexane/chloroform). As a result of mass spectrometric analysis, revealed was a fraction containing a mixture of cyclic phenol sulfides represented by formula (3) wherein n was from 5 to 12. This fraction was separated into individual compounds by gel permeation chromatography (chloroform) to obtain 0.97 g of the cyclic phenol compound represented by formula (3) wherein n=8, m=1, Y$_2$=tert-butyl, that is, 5, 11, 17, 23, 29, 35, 41, 47-octa-tert-butyl-49, 50, 51, 52, 53, 54, 55, 56-octahydroxy-2, 8, 14, 20, 26, 32, 38, 44-octathia-[43.3.1.1$^{3,7}$1$^{9,13}$1$^{15,19}$1$^{21,25}$1$^{27,31}$1$^{33,37}$1$^{39,43}$]hexapentaconta-1-(49), 3, 5, 7(56), 9, 11, 13(55), 15, 17, 19(54), 21, 23, 25(53), 27, 29, 31(52), 33, 35, 37(51), 39, 41, 43(50), 45, 47-tetracosaene (XIII).

Analytical data for reaction product (XIII) are given below.

MS m/z: 1440 (M$^+$)

Elemental analysis, % Calculated for $C_{80}H_{96}O_8S_8$: C, 66.62; H, 6.71; S, 17.79 Found: C, 66.25; H, 6.67; S, 17.20

Application Example 1

A solution in an organic solvent of 25, 26, 27, 28-tetraacetoxy-5, 11, 17, 23-tetra-tert-butyl-2, 8, 14, 20-tetrathia[19.3.1.1$^{3,7}$1$^{9,13}$1$^{15,19}$]octacosa-1(25), 3, 5, 7(28), 9, 11 13(27), 15, 17, 19(26), 21, 23-dodecaene (VI) produced in Example 6 was brought into contact with an aqueous solution containing Na ions to conduct Na ion extraction.

Into 20 ml of ether was dissolved 7.64 mg of cyclic phenol sulfide (VI). This solution was introduced into a 100-ml separatory funnel along with 20 ml of an aqueous solution containing Na ions in a concentration of 10 ppm, and this funnel was shaken for 5 hours. For the purpose of comparison, a mixture of 20 ml of ether not containing cyclic phenol sulfide (VI) and 20 ml of the aqueous solution containing Na ions in a concentration of 10 ppm was likewise shaken for 5 hours. The two samples were allowed to stand for 30 minutes, and the ion concentration in each aqueous solution was then measured with an ion-selective electrode.

As a result, the aqueous solution in the treated sample containing cyclic phenol sulfide (VI) had a lower Na ion concentration than the aqueous solution in the treated sample not containing cyclic phenol sulfide (VI), with the difference in Na ion concentration between the two solutions being 31.6% of the Na ion concentration in the latter solution.

The above results show that by contacting the aqueous phase containing Na ions with the organic phase containing cyclic phenol sulfide (VI), Na ions could be extracted into the organic phase.

Application Example 2

5, 11, 17, 23-Tetra-tert-butyl-25, 26, 27, 28-tetrahydroxy-2, 8, 14, 20-tetrathia[19.3.1.1$^{3,7}$1$^{9,13}$1$^{15,19}$]octacosa-1(25), 3, 5, 7(28), 9, 11, 13(27), 15, 17, 19(26), 21, 23-dodecaene (I) produced in Example 1 was added in a small amount to a gasoline to evaluate oxidative stability through an induction period test (in accordance with GM6141-M) as follows.

To a cracking gasoline containing a antioxidant of phenol and amine in an amount of 50 ppm was added cyclic phenol sulfide (I) in an amount of 10 ppm. An induction period test was performed in the presence of Cu ions in an amount of 2 ppm under conditions of an oxygen pressure of 7 kg/cm$^2$ and a temperature of 100° C. The time period to an inflection point in regard to oxygen pressure decrease was determined as an induction period. For the purpose of comparison, a cracking gasoline containing the antioxidant of phenol and amine only in an amount of 50 ppm was used as Comparative Sample 1, and a cracking gasoline containing the antioxidant of phenol and amine in a larger amount of 100 ppm was used as Comparative Sample 2.

As a result, the sample containing cyclic phenol sulfide (I) in an amount of 10 ppm had an induction period as long as 190 minutes, whereas Comparative Samples 1 and 2 had far shorter induction periods of 60 minutes and 70 minutes, respectively.

The above results show that the cyclic phenol sulfide is effective in improving oxidative stability.

While the invention has been described in detail and with reference to specific embodiments thereof, it will be apparent to one skilled in the art that various changes and modifications can be made therein without departing from the spirit and scope thereof.

What is claimed is:

1. A cyclic phenol sulfide represented by the following formula (1):

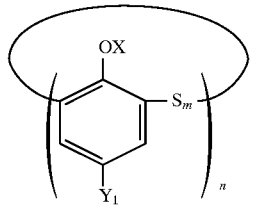

(1)

wherein X represents a hydrocarbon group, or an acyl group;

$Y_1$ represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$, in which $R^1$, $R^2$, $R^3$, $R^4$, $R^5$, $R^6$, and $R^7$ each represents a hydrogen atom or a hydrocarbon group;

n is an integer of 4 or more; and m is an integer of 1 to 7, provided that the plural m's of the $S_m$'s are the same or different;

the plural X's are the same or different; and the plural $Y_1$'s are the same or different.

2. The cyclic phenol sulfide as claimed in claim 1, wherein the hydrocarbon group represented by X, $Y_1$, $R^1$, $R^2$, $R^3$, $R^4$, $R^5$, $R^6$, or $R^7$ is selected from the group consisting of a saturated aliphatic hydrocarbon group, an unsaturated aliphatic hydrocarbon group, an alicyclic hydrocarbon group, an alicyclic-aliphatic hydrocarbon group, an aromatic hydrocarbon group, and an aromatic-aliphatic hydrocarbon group.

3. A cyclic phenol sulfide represented by the following formula (1):

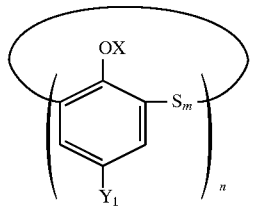

(1)

wherein X represents a hydrogen atom, a hydrocarbon group, or an acyl group;

wherein $Y_1$ represents a halogenated hydrocarbon group selected from the group consisting of a halogenated saturated aliphatic hydrocarbon group, a halogenated alicyclic hydrocarbon group, a halogenated alicyclic-aliphatic hydrocarbon group, a halogenated aromatic hydrocarbon group, and a halogenated aromatic-aliphatic hydrocarbon group;

n is an integer of 3 or more; and m is an integer of 1 to 7, provided that the plural m's of the $S_m$'s are the same or different;

the plural X's are the same or different; and the plural $Y_1$'s are the same or different.

4. The cyclic phenol sulfide as claimed in claim 1, wherein m is an integer of 1 to 5.

5. A process for producing a cyclic phenol sulfide represented by the following formula (3):

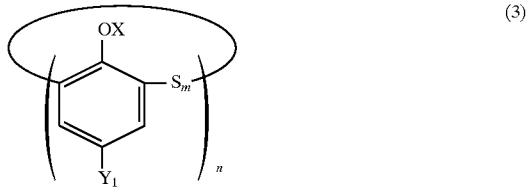

(3)

wherein $Y_2$ represents a hydrogen atom or a hydrocarbon group;

n is an integer of 3 or more; and m is an integer of 1 to 7, provided that the plural m's of the $S_m$'s are the same or different; and the plural $Y_2$'s are the same or different, which comprises a step of reacting a phenol represented by the following formula (2) with at least 0.1 gram equivalent of elemental sulfur in the presence of at least 0.005 gram equivalent of at least one metal reagent selected from the group consisting of alkali metal reagents and alkaline-earth metal reagents, each per gram equivalent of the phenol represented by formula (2):

(2)

wherein said step of reacting a phenol is conducted while removing water and hydrogen sulfide.

6. The process as claimed in claim 5, wherein the elemental sulfur is used in an amount of 0.35 gram equivalent or more per gram equivalent of the phenol represented by formula (2).

7. The process as claimed in claim 5, wherein the elemental sulfur is used in an amount of 20 gram equivalent or less per gram equivalent of the phenol represented by formula (2).

8. The process as claimed in claim 5, wherein the alkali metal reagents are selected from the group consisting of elemental lithium metal, elemental sodium metal, elemental potassium metal, lithium hydride, sodium hydride, potassium hydride, lithium hydroxide, sodium hydroxide, potassium hydroxide, rubidium hydroxide, cesium hydroxide, lithium carbonate, sodium carbonate, potassium carbonate, rubidium carbonate, cesium carbonate, sodium butoxide, sodium ethoxide, lithium butoxide, lithium ethoxide, potassium butoxide, and potassium ethoxide.

9. The process as claimed in claim 5, wherein the alkaline-earth metal reagents are selected from the group consisting of elemental calcium metal, elemental magnesium metal, calcium hydride, calcium oxide, barium oxide, magnesium oxide, strontium oxide, calcium hydroxide, barium hydroxide, magnesium hydroxide, strontium hydroxide, calcium carbonate, barium carbonate, strontium carbonate, magnesium methoxide, and magnesium ethoxide.

10. The process as claimed in claim 5, wherein the metal reagent is used in an amount of 0.01 gram equivalent or more per gram equivalent of the phenol represented by formula (2).

11. The process as claimed in claim 5, wherein the metal reagent is used in an amount of 10 gram equivalent or less per gram equivalent of the phenol represented by formula (2).

12. The process as claimed in claim 5, wherein the step of reacting is conducted in an inert gas atmosphere.

13. The process as claimed in claim 5, wherein the step of reacting is conducted at a temperature of 130° C. or more.

14. The process as claimed in claim 5, wherein the step of reacting is conducted at a temperature of 300° C. or less.

15. The process as claimed in claim 5, wherein the reaction is conducted using as a solvent at least one selected from the group consisting of an aliphatic hydrocarbon, an aromatic hydrocarbon, an ether, a sulfide, and a dihydric alcohol.

16. The process as claimed in claim 5, wherein the hydrocarbon group represented by $Y_2$ is selected from the group consisting of a saturated aliphatic hydrocarbon group, an unsaturated aliphatic hydrocarbon group, an alicyclic hydrocarbon group, an alicyclic-aliphatic hydrocarbon group, an aromatic hydrocarbon group, and an aromatic-aliphatic hydrocarbon group.

17. The process as claimed in claim 5, wherein the compound represented by formula (3) is further converted to a compound represented by the following formula (1):

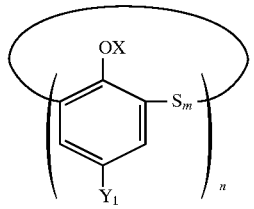

(1)

wherein X represents a hydrogen atom, a hydrocarbon group, or an acyl group;

$Y_1$ represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$, in which $R^1$, $R^2$, $R^3$, $R^4$, $R^5$, $R^6$, and $R^7$ each represents a hydrogen atom or a hydrocarbon group;

n is an integer of 3 or more; and m is an integer of 1 to 7, provided that the plural m's of the $S_m$'s are the same or different;

the plural X's are the same or different; and the plural $Y_1$'s are the same or different.

18. A cyclic phenol sulfide represented by the following formula (1):

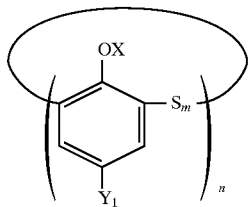

(1)

wherein X represents a hydrogen atom;

$Y_1$ represents a hydrogen atom, a hydrocarbon group, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$, in which $R^1$, $R^2$, $R^3$, $R^4$, $R^5$, $R^6$, and $R^7$ each represents a hydrogen atom or a hydrocarbon group;

n is an integer of 5 or more; and m is an integer of 1 to 7, provided that the plural m's of the $S_m$'s are the same or different;

the plural X's are the same or different; and the plural $Y_1$'s are the same or different.

19. A cyclic phenol sulfide represented by the following formula (1):

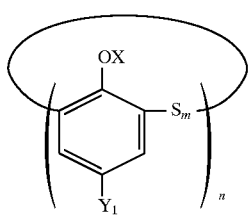

(1)

wherein X represents a hydrogen atom, a hydrocarbon group, or an acyl group;

$Y_1$ represents a hydrogen atom, a methyl group, an isopropyl group, a neopentyl group, an n-hexyl group, a tert-octyl group, an isononyl group, a vinyl group, an allyl group, a cyclohexyl group, a 4-methylcyclohexenyl group, a phenyl group, a naphthyl group, a benzyl group, a hydrocarbon group derived from a polymer or copolymer of ethylene, propylene, butylene, acetylene, butadiene or isoprene, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$, in which $R^1$, $R^2$, $R^3$, $R^4$, $R^5$, $R^6$, and $R^7$ each represents a hydrogen atom or a hydrocarbon group;

n is an integer of 4; and m is an integer of 1 to 7, provided that the plural m's of the $S_m$'s are the same or different;

the plural X's are the same or different; and the plural $Y_1$'s are the same or different.

20. The process as claimed in claim 5, wherein the at least one alkali metal reagent is selected from the group consisting of lithium hydride, sodium hydride, lithium hydroxide, sodium hydroxide, potassium hydroxide, rubidium hydroxide, cesium hydroxide, sodium butoxide, sodium ethoxide, and potassium butoxide.

21. A cyclic phenol sulfide represented by the following formula (1):

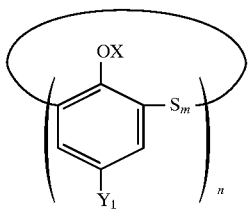
(1)

wherein X represents a hydrogen atom or an acyl group;

$Y_1$ represents a hydrogen atom, an isopropyl group, an n-butyl group, an isobutyl group, a tert-butyl group, a neopentyl group, an n-hexyl group, a tert-octyl group, an isononyl group, a vinyl group, an allyl group, a cyclohexyl group, a 4-methylcyclohexyl group, a phenyl group, a naphthyl group, a benzyl group, a hydrocarbon group derived from a polymer or copolymer of ethylene, propylene, butylene, acetylene, butadiene or isoprene, a halogenated hydrocarbon group, —$COR^1$, —$OR^2$, —$COOR^3$, —CN, —$CONH_2$, —$NO_2$, —$NR^4R^5$, a halogen atom, —$SO_4R^6$, or —$SO_3R^7$, in which $R^1$, $R^2$, $R^3$, $R^4$, $R^5$, $R^6$ and $R^7$ each represents a hydrogen atom or a hydrocarbon group;

n is an integer of 3; and m is an integer of 1 to 7, provided that the plural m's of the Sm's are the same or different.

22. The cyclic phenol sulfide as claimed in claim 3, wherein the hydrocarbon group represented by X is selected from the group consisting of a saturated aliphatic hydrocarbon group, an unsaturated aliphatic hydrocarbon group, an alicyclic hydrocarbon group, an alicyclic-aliphatic hydrocarbon group, an aromatic hydrocarbon group, and an aromatic-aliphatic hydrocarbon group.

23. The cyclic phenol sulfide as claimed in claim 18, wherein the hydrocarbon group represented by $Y_1$, $R^1$, $R^2$, $R^3$, $R^4$, $R^5$, $R^6$, and $R^7$ is selected from the group consisting of a saturated aliphatic hydrocarbon group, an unsaturated aliphatic hydrocarbon group, an alicyclic hydrocarbon group, an alicyclic-aliphatic hydrocarbon group, an aromatic hydrocarbon group, and an aromatic-aliphatic hydrocarbon group.

24. The cyclic phenol sulfide as claimed in claim 19, wherein the hydrocarbon group represented by $X_1$, $Y_1$, $R^1$, $R^2$, $R^3$, $R^4$, $R^5$, $R^6$, and $R^7$ is selected from the group consisting of a saturate aliphatic hydrocarbon group, an unsaturated aliphatic hydrocarbon group, an alicyclic hydrocarbon group, an alicyclic-aliphatic hydrocarbon group, an aromatic hydrocarbon group, and an aromatic-aliphatic hydrocarbon group.

25. The cyclic phenol sulfide as claimed in claim 21, wherein the hydrocarbon group represented by $R_1$, $R^2$, $R^3$, $R^4$, $R^5$, $R^6$, and $R^7$ is selected from the group consisting of a saturated aliphatic hydrocarbon group, an unsaturated aliphatic hydrocarbon group, an alicyclic hydrocarbon group, an alicyclic-aliphatic hydrocarbon group, an aromatic hydrocarbon group, and an aromatic-aliphatic hydrocarbon group.

26. The cyclic phenol sulfide as claimed in claim 3, wherein m is an integer of 1 to 5.

27. The cyclic phenol sulfide as claimed in claim 18, wherein m is an integer of 1 to 5.

28. The cyclic phenol sulfide as claimed in claim 19, wherein m is an integer of 1 to 5.

29. The cyclic phenol sulfide as claimed in claim 21, wherein m is an integer of 1 to 5.

* * * * *